United States Patent
Hart et al.

(10) Patent No.: US 7,625,370 B2
(45) Date of Patent: Dec. 1, 2009

(54) TISSUE FUSION/WELDER APPARATUS AND METHOD

(75) Inventors: Charles C. Hart, Summerville, SC (US); Gary M. Johnson, Mission Viejo, CA (US); Said S. Hilal, Coto de Caza, CA (US); John R. Brustad, Dana Point, CA (US); Edward D. Pingleton, San Juan Capistrano, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 835 days.

(21) Appl. No.: 10/504,279

(22) PCT Filed: Jan. 16, 2003

(86) PCT No.: PCT/US03/01586

§ 371 (c)(1),
(2), (4) Date: Aug. 11, 2004

(87) PCT Pub. No.: WO03/068046

PCT Pub. Date: Aug. 21, 2003

(65) Prior Publication Data

US 2005/0165444 A1   Jul. 28, 2005

(51) Int. Cl.
*A61B 18/18*   (2006.01)
*A61B 17/08*   (2006.01)

(52) U.S. Cl. .................. 606/27; 606/214; 606/49
(58) Field of Classification Search ............. 606/27–31, 606/41, 48–52, 213–216
See application file for complete search history.

(56) References Cited

U.S. PATENT DOCUMENTS

| | | |
|---|---|---|
| 4,041,952 A | 8/1977 | Morrison, Jr. et al. |
| 5,151,102 A | 9/1992 | Kamiyama et al. |
| 5,207,691 A | 5/1993 | Nardella |
| 5,403,312 A | 4/1995 | Yates et al. |
| 5,443,463 A | 8/1995 | Stern et al. |
| 5,458,598 A | 10/1995 | Feinberg et al. |
| 5,531,744 A | 7/1996 | Nardella et al. |
| 5,571,216 A * | 11/1996 | Anderson .................. 128/898 |
| 5,573,535 A | 11/1996 | Virklund |
| 5,665,085 A | 9/1997 | Nardella |
| 5,665,100 A | 9/1997 | Yoon |

(Continued)

FOREIGN PATENT DOCUMENTS

WO    WO 02/085218    10/2002

OTHER PUBLICATIONS

European Patent Office, Supplementary Partial European Search Report for European Patent Application No. 03710688.7, dated Aug. 13, 2009, entitled Tissue Fusion/Welder Apparatus and Method.

*Primary Examiner*—Michael Peffley
(74) *Attorney, Agent, or Firm*—John F. Heal; Patrick Y. Ikehara; Richard L. Myers

(57) ABSTRACT

A tissue welding apparatus is adapted to fuse a first piece of tissue to a second piece of tissue which are disposed in a surface proximate relationship. An elongate shaft carries a first jaw, and a second opposing jaw moveable relative to the first jaw. At least one penetrating member is carried by the first jaw and moveable relative to the second jaw to create a channel through the first piece of material and the second piece of material. A source of heat is coupled to the penetrating member for denaturing the tissue defining the channel. This denatured tissue forms a column binding the first piece of tissue to the second piece of tissue. A chemical agent can be carried to the tissue with the penetrating member.

60 Claims, 17 Drawing Sheets

U.S. PATENT DOCUMENTS

| | | |
|---|---|---|
| 5,674,220 A | 10/1997 | Fox et al. |
| 5,688,270 A | 11/1997 | Yates et al. |
| 5,709,680 A | 1/1998 | Yates et al. |
| 5,810,811 A | 9/1998 | Yates et al. |
| 5,833,690 A | 11/1998 | Yates et al. |
| 5,876,401 A | 3/1999 | Schulze et al. |
| 5,891,142 A | 4/1999 | Eggers et al. |
| 5,908,420 A | 6/1999 | Parins et al. |
| 5,925,078 A | 7/1999 | Anderson |
| 6,010,516 A | 1/2000 | Hulka |
| 6,030,384 A | 2/2000 | Nezhat |
| 6,083,223 A * | 7/2000 | Baker .......................... 606/52 |
| 6,086,586 A * | 7/2000 | Hooven ....................... 606/50 |
| H1904 H | 10/2000 | Yates |
| 6,126,658 A | 10/2000 | Baker |
| 6,152,923 A | 11/2000 | Ryan |
| 6,162,220 A * | 12/2000 | Nezhat ........................ 606/48 |
| 6,174,309 B1 | 1/2001 | Wrublewski et al. |
| 6,183,490 B1 * | 2/2001 | Korbar et al. ............... 606/188 |
| 6,302,898 B1 * | 10/2001 | Edwards et al. ............. 606/214 |
| 6,770,070 B1 * | 8/2004 | Balbierz ...................... 606/41 |

\* cited by examiner

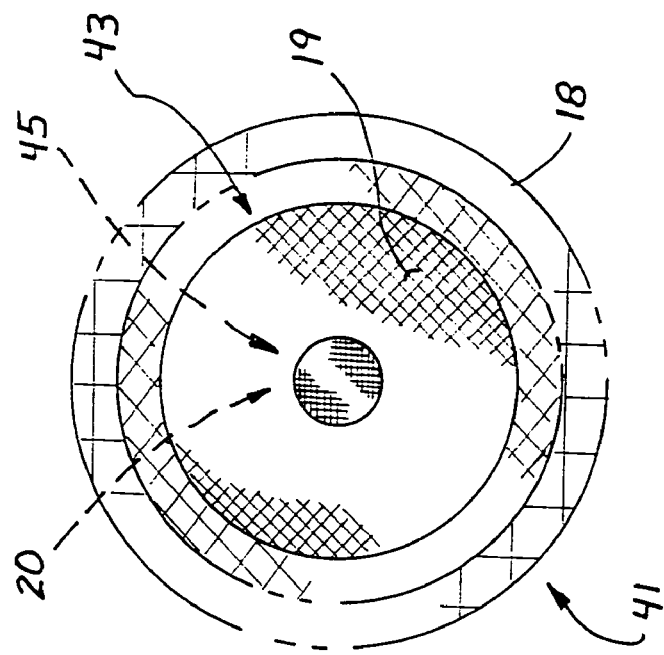
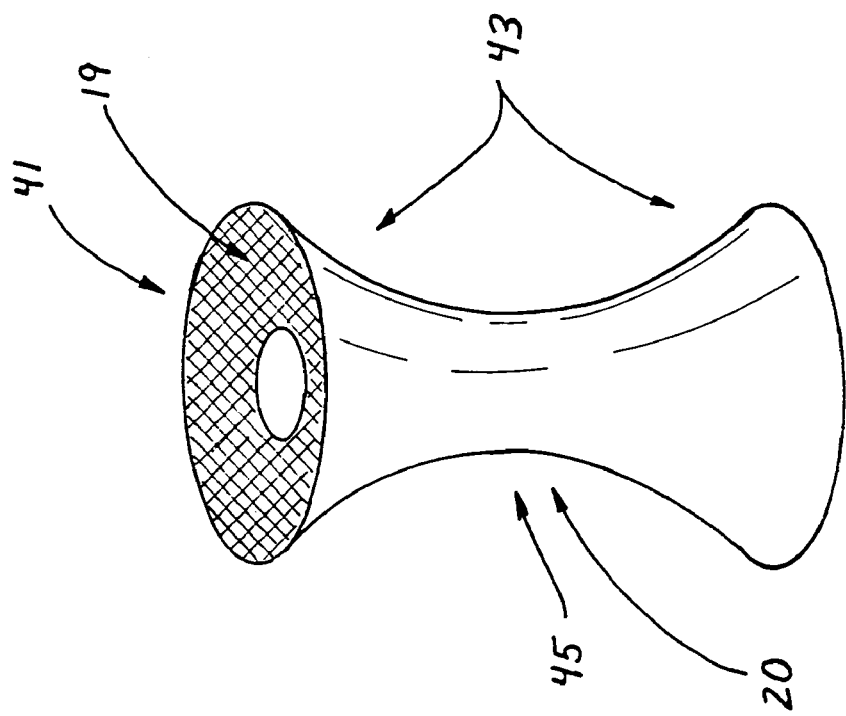
Fig. 12
Fig. 11

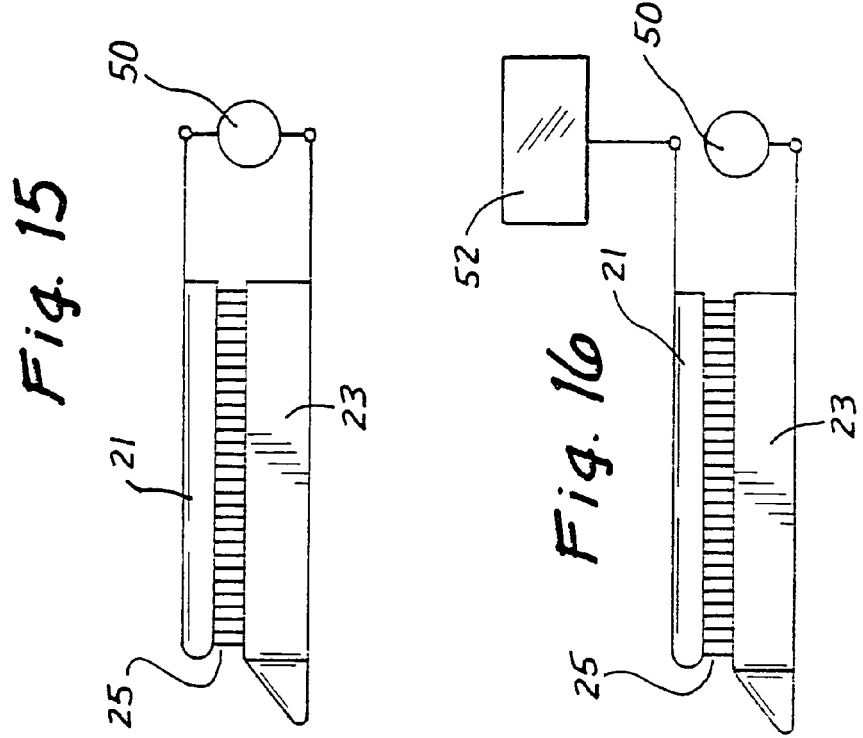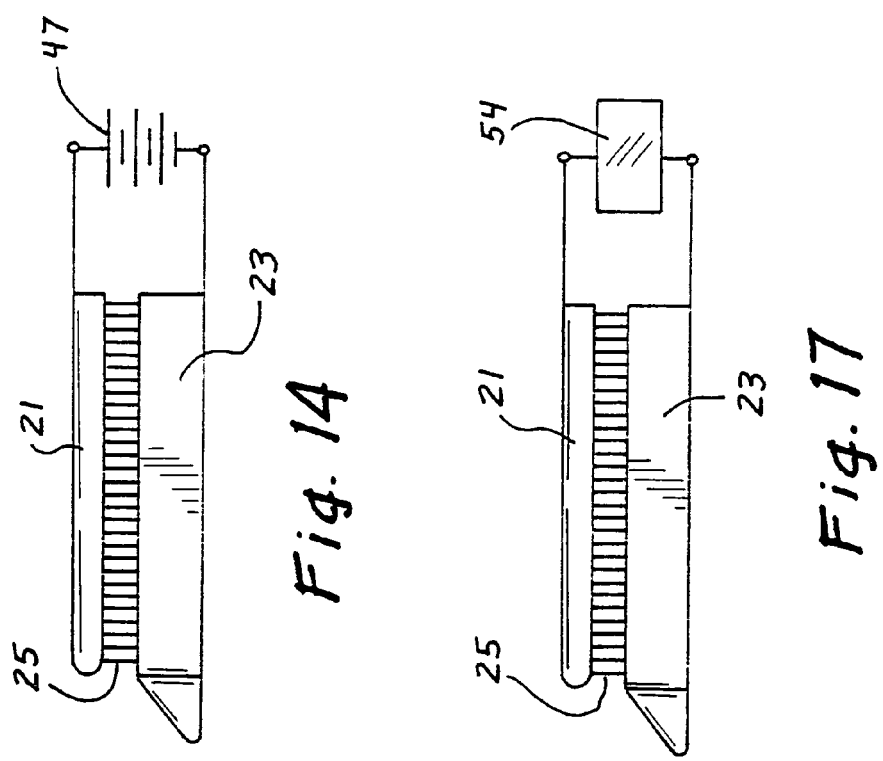

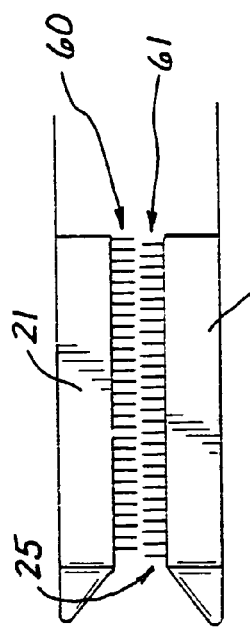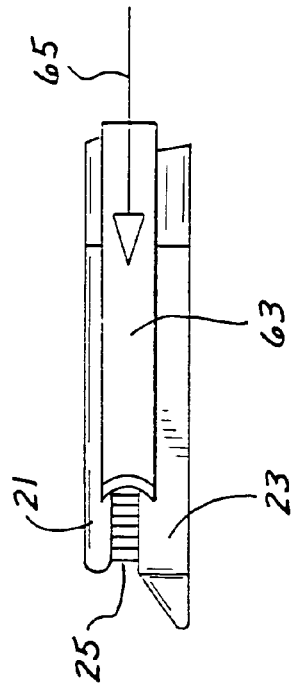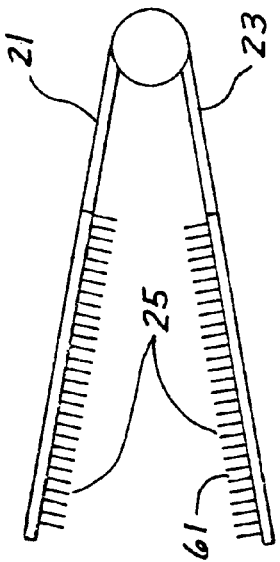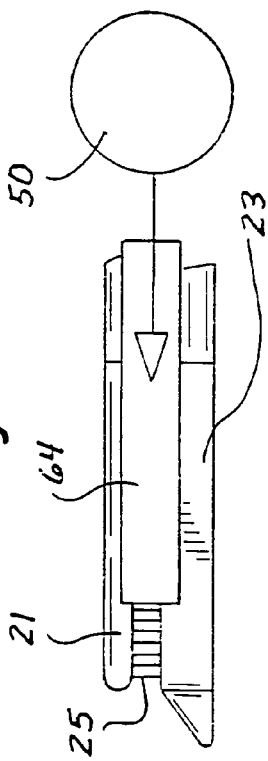

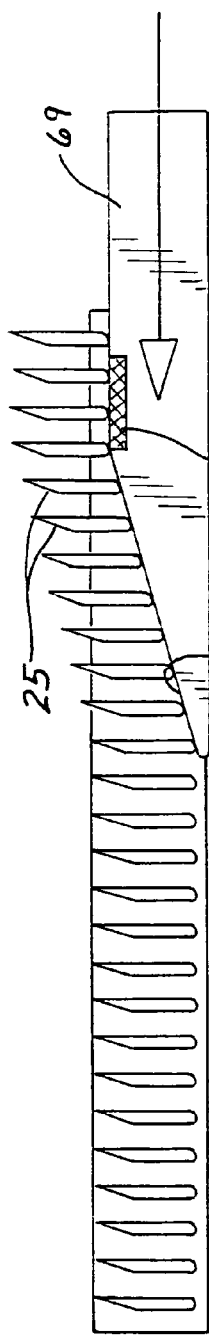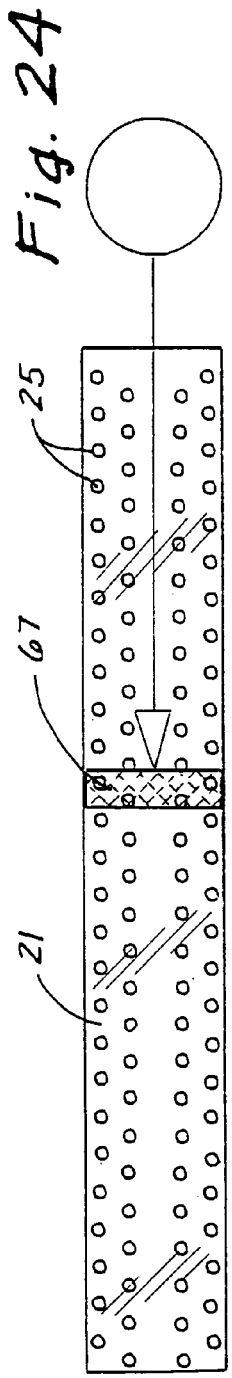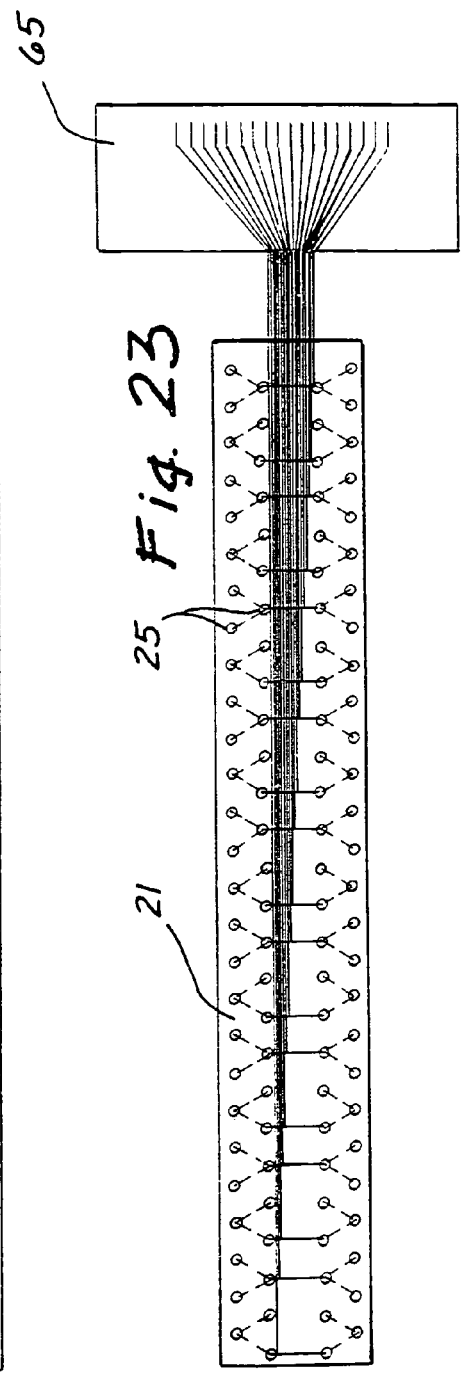

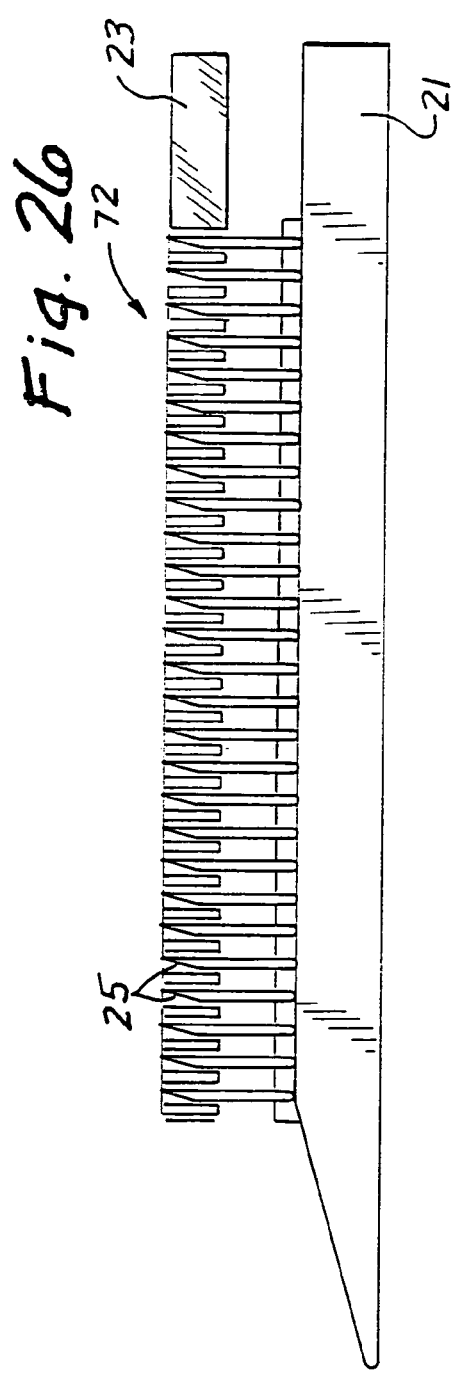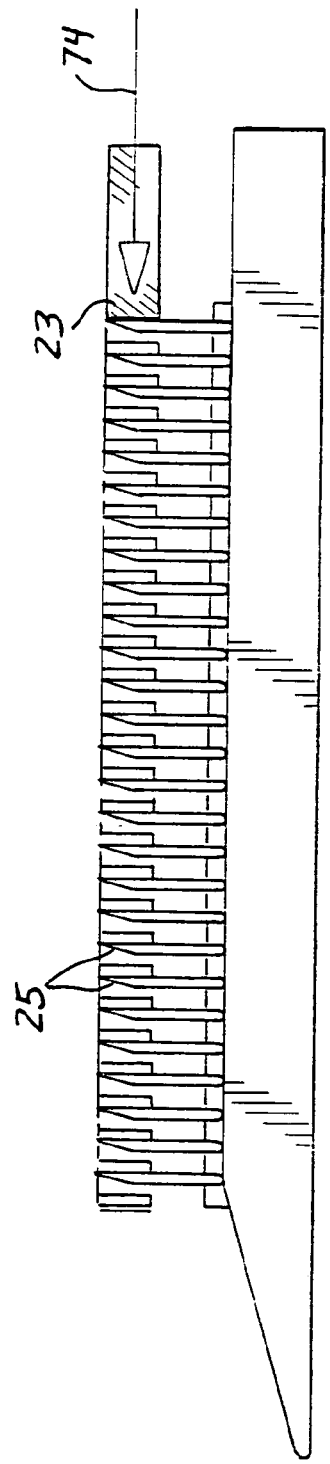

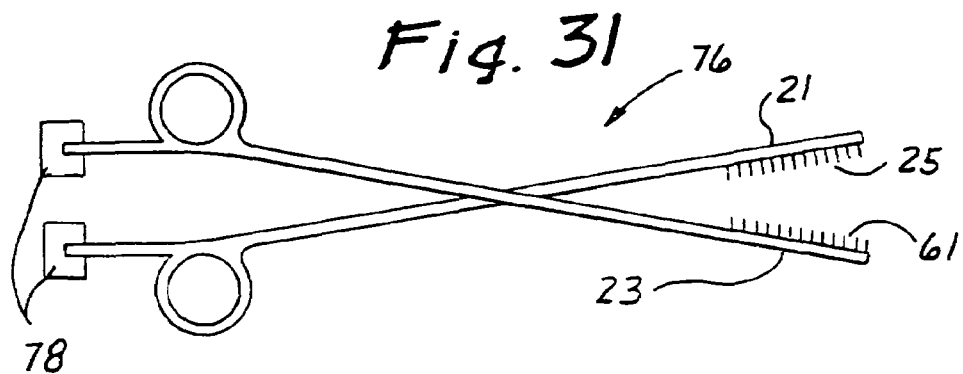
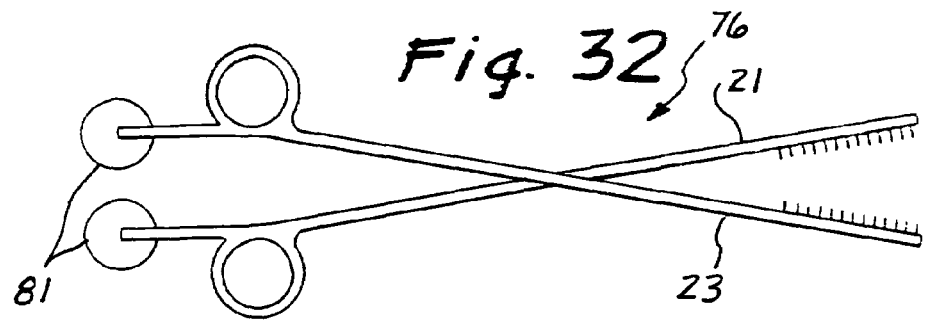
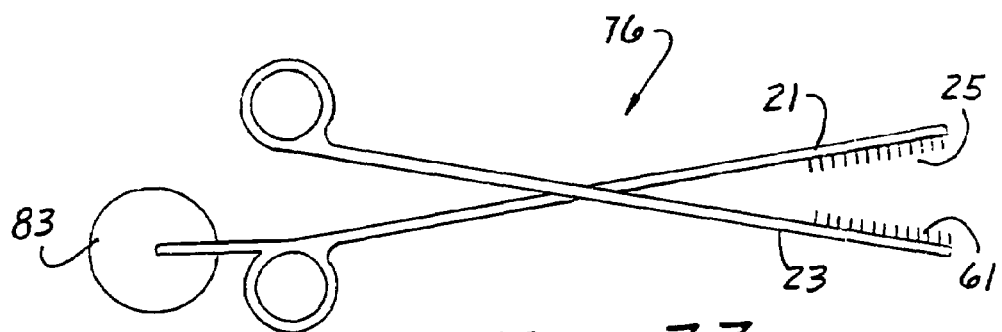
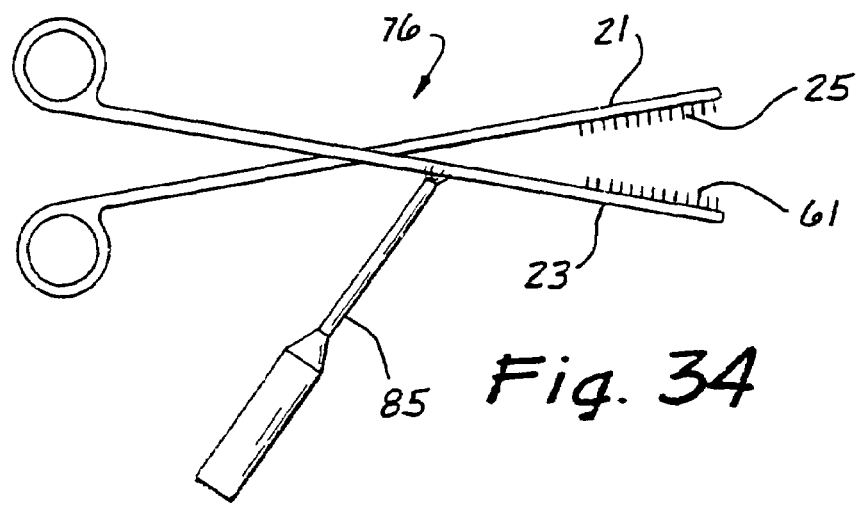

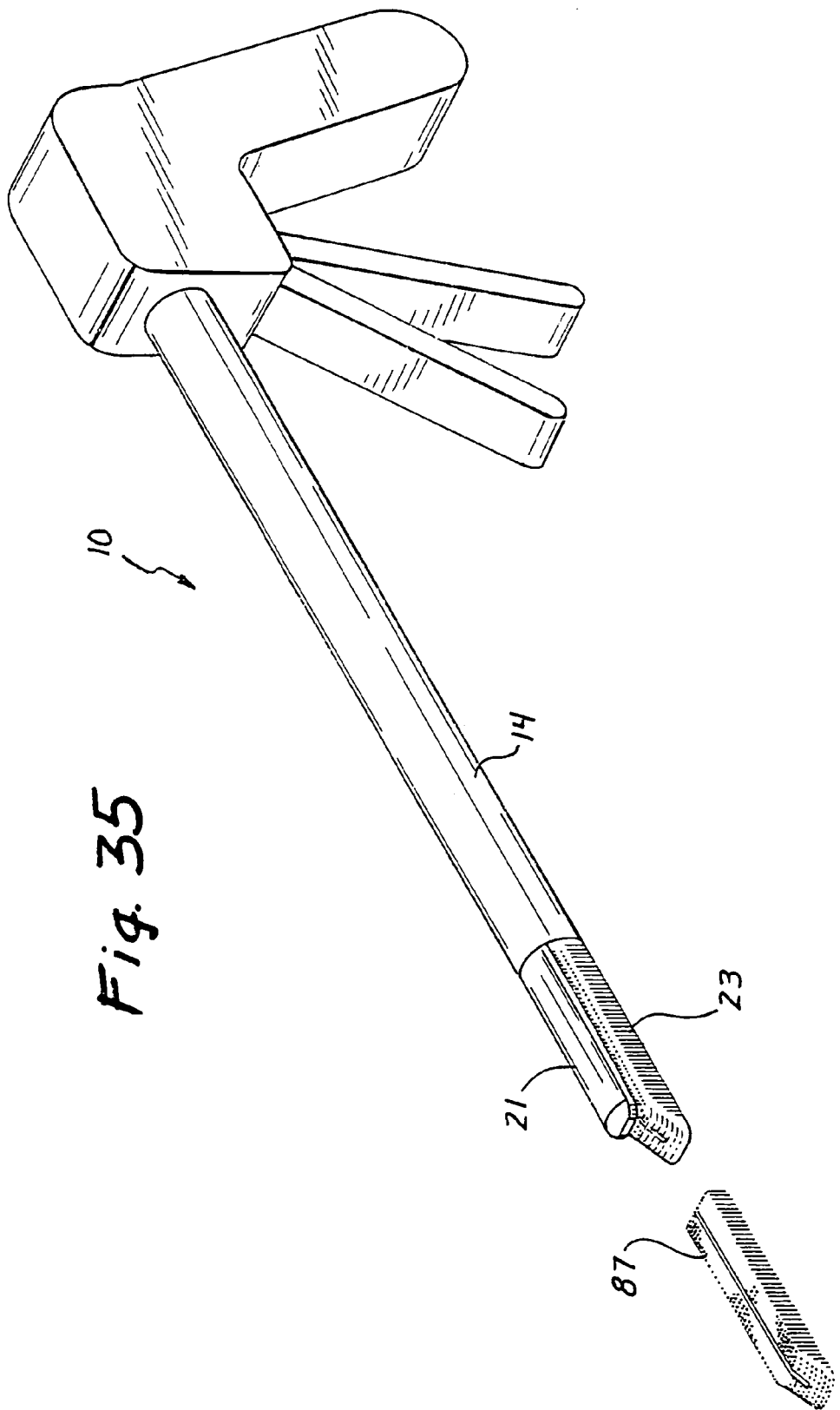

TISSUE FUSION/WELDER APPARATUS AND METHOD

BACKGROUND OF THE INVENTION

1. Field of the Invention

This invention generally relates to surgical devices and, in particular, to an apparatus and method for fusing and/or welding tissue.

2. Discussion of Related Art

Surgery generally involves the cutting and fixing of tissue. The cutting is usually undertaken in one of two modalities, either cold cutting or hot cutting. Cold cutting is performed using a mechanical device such as a knife or scissors. Hot cutting involves the use of high frequency electrosurgical current, ultrasonic sound or heat. The fixation of cut tissue commonly involves the use of sutures, staples or clips. More recently, tissue adhesives have evolved as an occasional alternative.

The process of inhibiting blood flow from cut or severed tissue, commonly referred to as hemostasis, is often undertaken using power generated by an electrosurgical device. Various electrosurgical effects can be achieved, such as coagulation, fulguration and cauterization. Coagulation makes use of high frequency electrosurgical waveforms that are designed to desiccate tissue by vaporizing the cellular content and thereby restricting the flow of blood from the site. Fulguration is a form of coagulation that is more broadly applied to provide hemostasis over large areas. Cauterization is a well-known form of hemostasis and has been used for many years. A hot instrument applied to a portion of the severed or damaged tissue will normally arrest blood flow. The application of heat to the tissue fuses the cellular content and actually welds cellular content in a manner somewhat similar to metal welding.

Several procedures have evolved which use devices that provide both cutting and fixation in a single instrument. The most common of these devices comprises a surgical stapler that places two rows of titanium surgical staples and subsequently cuts the tissue between the rows. These devices are often referred to as "take-down" devices. They are used to divide body passages and provide concomitant fluid stasis.

An example of such devices is the commonly available gastro-intestinal anastamosis (GIA) type stapler. It comprises a jaw fitted with a cartridge holding four to six rows of staples in a deployable position, a hinged anvil sized and configured to deform the staples of the cartridge, and a shaft communicating with a handle held by a user. In use, the device is placed along, and compressed upon, a portion of tissue to be cut and stapled. The staples are subsequently urged through the tissue and against the anvil where they are deformed into a preferred folded-over condition. A sharp surgical blade is then moved forward between rows of staples to divide the tissue. Fluid stasis is accomplished by the overlapping rows of folded-over and compressed staples.

As one would imagine, it is not desirable to over-compress tissue or develop a condition where required nourishment to tissue is compromised. If too many staples are placed or if the staples are over-compressed, the included tissue may be deprived of nutrition and may subsequently necrose and cause serious complications. In addition, staples are typically formed of a material which is foreign to the body and may cause responses that will further complicate recovery or healing. Staples cannot be cut through or removed easily. Staples also cause problems with imaging technologies. They may show up as artifacts in MRI, CT scans and fluoroscopy.

Surgical clips are often used to occlude small vessels. They normally comprise a C-shaped metallic member that is highly compressed upon tissue. Nourishment to the residual portion of "clipped-off" tissue is completely interrupted. Even when a divided or repaired portion of tissue is sutured, special care is taken not to place the suture too tightly so that nourishment to the residual portion is interrupted.

Tissue adhesives, which provide hemostasis as well as the "gluing" of tissue, have proven to be effective. However, they often require prior preparation from autologous materials. In addition, they do not have the full confidence of the medical community.

To avoid the complications of clips, staples, adhesives and sutures, attempts have been made to fuse or weld tissue. For instance, a vessel may be clamped tightly with a hemostat or grasper, and subsequently energized with an electrosurgical generator. This technique is commonly referred to as "buzzing the hemostat". The heat generated within the tissue may cause the proteins of the cellular content to fuse and create a fluid-tight arrangement.

This technique has proved to be relatively effective in small vessels; however, large vessels are not indicated for this approach. The relationship between the diameter of the vessel and the wall thickness has proven to be the limiting factor in tissue fusion and welding in most cases. Hemostatic graspers are available that compress tissue and apply an electrosurgical discharge that mimics the energized hemostat.

An electrosurgical generator is to supply a high voltage at a high frequency in order to produce an electric arc between an electrosurgical instrument and grounded tissue. This "electrosurgical effect" (ESE) is especially suited to cut and coagulate tissue in a quick and effective manner. However, the ESE is not effective to divide and provide hemostasis or fluid stasis in large vessels or conduits. While the ESE has been well adapted to seal small capillaries, it has not been effective to shut-off the fluid flow in a large conduit.

SUMMARY OF THE INVENTION

In view of the foregoing, the present invention comprises a device, and associated method, which is sized and configured to emulate the mechanical fixation of tissue. The present invention provides permanent fluid stasis in tissue by creating small, discrete tissue welds along a preferred pathway, and subsequently cutting relative to the welds. The welding or fusing of the tissue is accomplished by application of heat to selected and localized areas. In a preferred embodiment, a device according to the present invention may comprise an elongate shaft having a handle at the proximal end and a pair of jaws at the distal end. The jaws comprise a first portion having a plurality of penetrating electrodes or elements, and a second portion having an electrical contact/compression member.

With the intent of merely heating the tissue adjacent the electrodes, the jaws can be connected in an electrosurgical monopolar, bipolar or "quasi" bipolar configuration. The electrodes can also be energized with direct current or any other heating source, in order to achieve the desired heating and consequent fusing or welding of tissue.

In one aspect of the invention, the device includes a first member and a second member opposing the first member. The first member is sized and configured to push a plurality of needle electrodes or elements through the tissue, where they contact the second member thereby providing electrical continuity. Upon application of electrical or thermal energy, the tissue through which the electrodes have passed is heated to the point of desiccation and subsequent fusion of certain cellular components. The resulting fusion or weld is continuous through the layers of tissue and resembles a "rivet". A plurality of fusion "channels" arranged appropriately provides fluid stasis without the introduction of any foreign material.

In other aspects of the invention, the jaws can be provided by a hemostat; a chemical-releasing sleeve may also be employed. A device according to the present invention overcomes the limitations of existing devices by providing a multiple-use device as opposed to a single-fire or single-use device.

These and other features of the invention will become more apparent with a discussion of the various embodiments in reference to the associated drawings.

DESCRIPTION OF THE DRAWINGS

The accompanying drawings, which are included in and constitute a part of this specification, illustrate the embodiments of the invention and, together with the description, explain the features and principles of the invention. In the drawings:

FIG. 11 is a perspective view of a fusion area produced by an embodiment of the present invention;

FIG. 12 is a top plan view of the fusion area shown in FIG. 11;

FIG. 14 is a side elevation view of a distal jaw portion comprising a direct current power source;

FIG. 15 is a side elevation view of a distal jaw portion comprising a bipolar electrosurgical power source;

FIG. 16 is a side elevation view of a distal jaw portion comprising a "quasi" bipolar electrosurgical power source;

FIG. 17 is a side elevation view of the distal jaw portion comprising a direct heat source;

FIG. 19 is a side elevation view of a distal jaw portion configured with electrodes on both opposed jaw portions;

FIG. 20 is a side elevation view of a distal jaw portion having a mechanical cutting member;

FIG. 21 is a side elevation view of a distal jaw portion having an electrosurgical cutting member;

FIG. 22 is a side elevation view of a distal jaw portion sized and configured to fit through a small-bore cannula;

FIG. 23 is a top plan schematic view of a solid-state electronic switching arrangement for energizing the electrodes of a distal jaw portion;

FIG. 24 is a top plan schematic view of a mechanical switching arrangement for energizing the electrodes of a distal jaw portion;

FIG. 25 is a side elevation schematic view of a sequential mechanical switching arrangement for lifting and energizing the electrodes of a distal jaw portion;

FIG. 26 is a side elevation schematic view of a distal jaw portion having a permeable anvil;

FIG. 27 is a side elevation schematic view of a distal jaw portion having a sliding contact permeable anvil;

FIG. 31 is a side elevation view of a hemostat having penetrating needles and being configured for operation in a monopolar electrosurgical configuration;

FIG. 32 is a side elevation view of a hemostat having penetrating needles and being configured in a bipolar electrosurgical configuration;

FIG. 33 is a side elevation view of a hemostat having penetrating needles and being configured in a direct heat configuration;

FIG. 34 is a side elevation view of a hemostat having penetrating needles and being configured for use with an external heat source;

FIG. 35 is a perspective view of a further embodiment of the invention having a chemical releasing sleeve;

DESCRIPTION OF THE INVENTION

Figure 1:
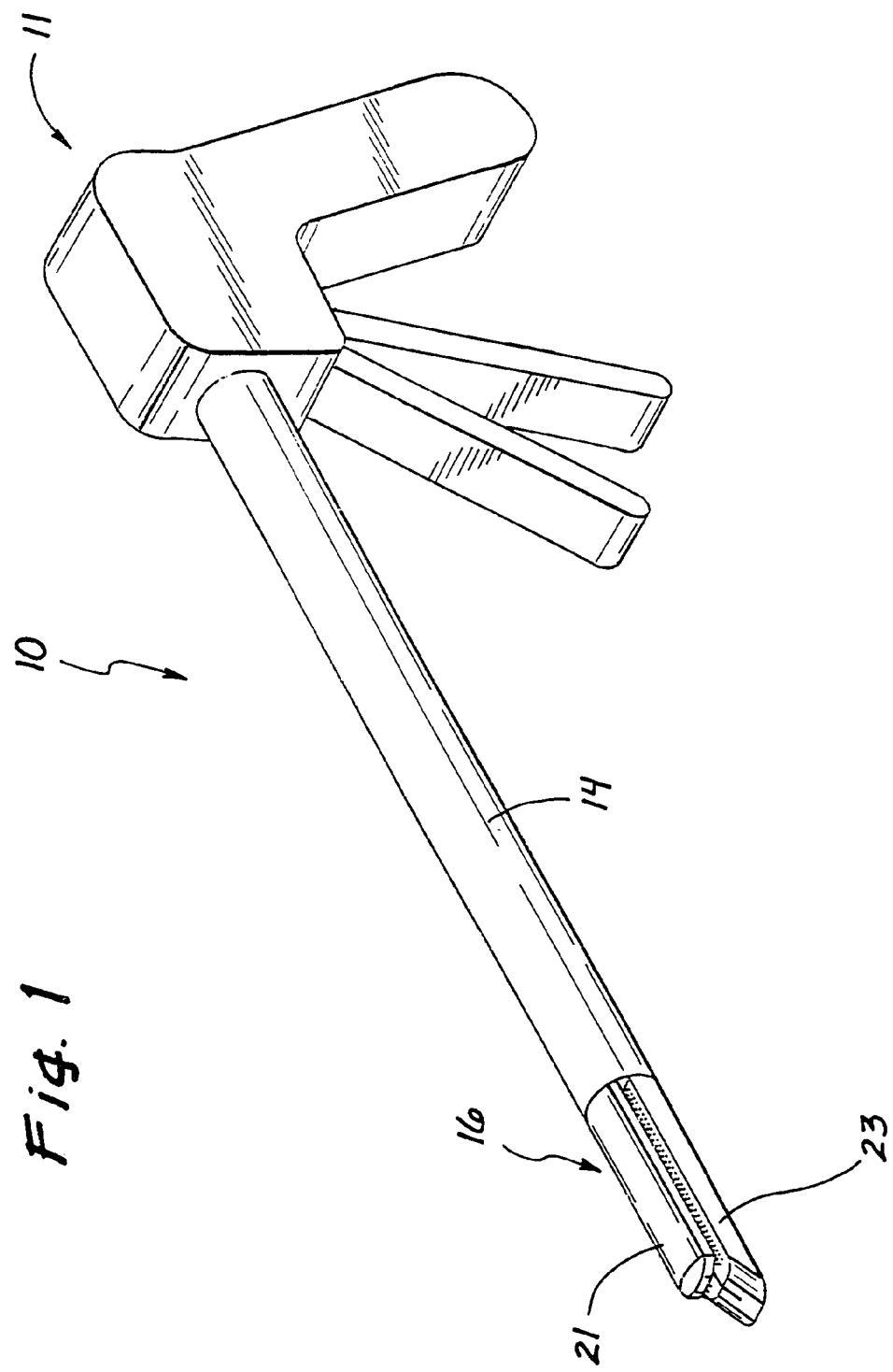
FIG. 1 is a perspective view of a laparoscopic device according to the present invention.
Figure 2:
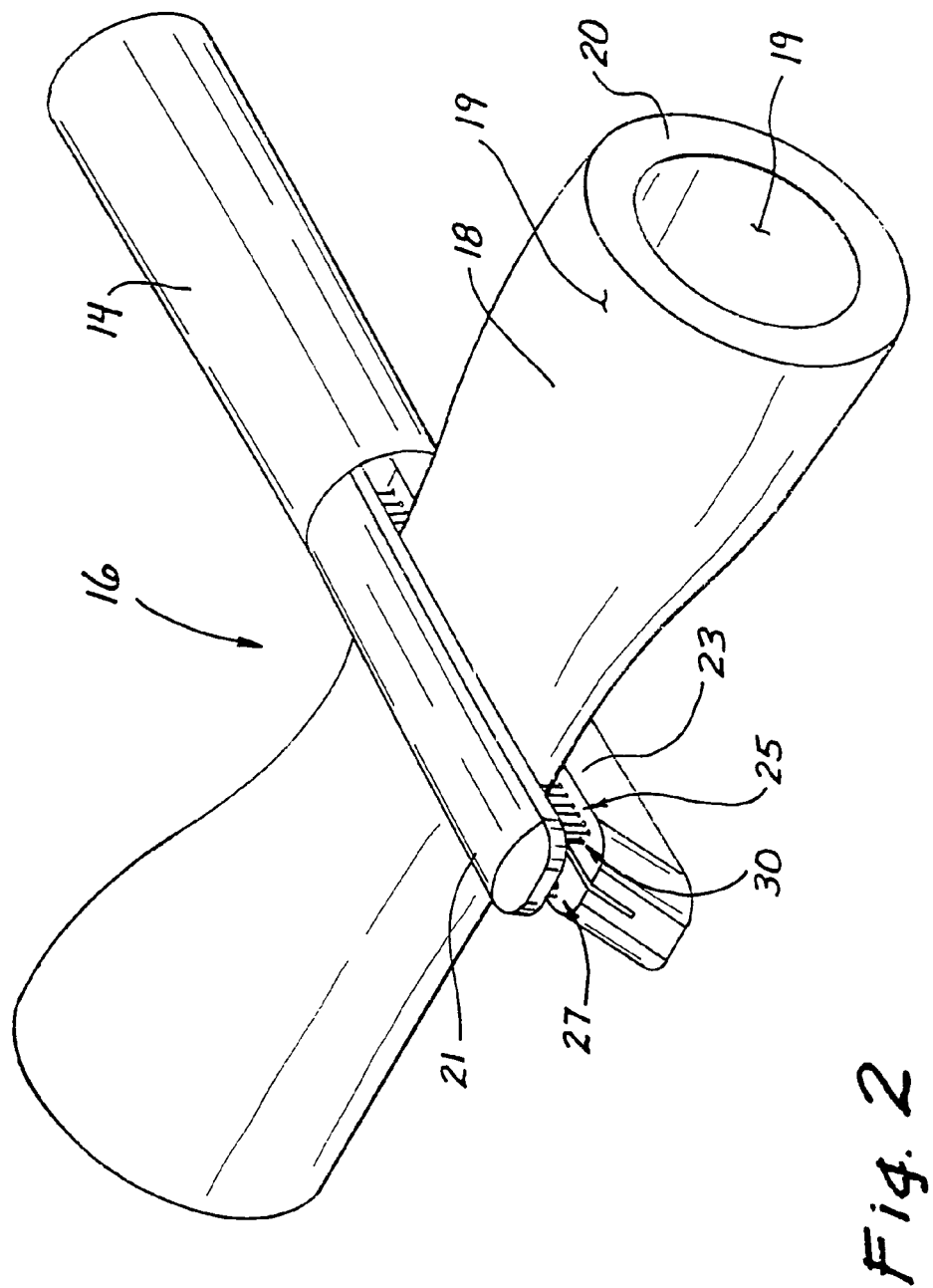
FIG. 2 is a perspective view of the distal portion of a laparoscopic device according to the present invention, in a closed condition with the tissue to be fused.
Figure 3:
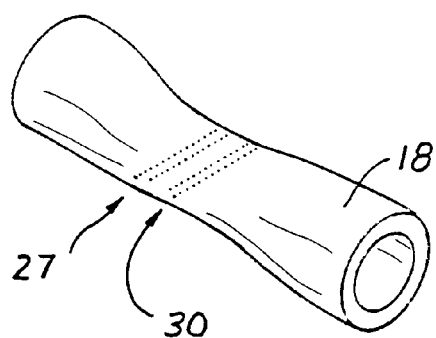
FIG. 3 is a perspective view of a portion of tissue that has been fused by the device of the present invention.
Figure 4:
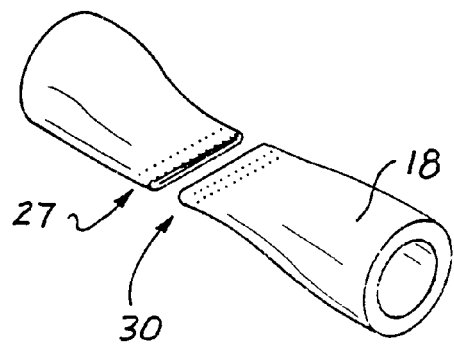
FIG. 4 is a perspective view of a portion of tissue that has been fused and divided by the device of the present invention.
Figure 6A:
FIG. 6A is an end elevation view of the distal portion of the device shown in FIG. 5A.
Figure 6B:
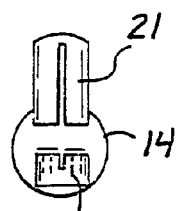
FIG. 6B is an end elevation view of the distal portion of the device shown in FIG. 5B.
Figure 6C:
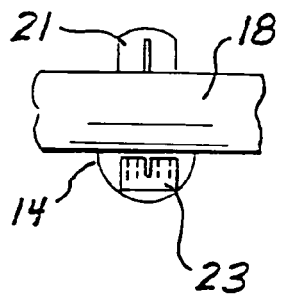
FIG. 6C is an end elevation view of the distal portion of the device shown in FIG. 5C.

With reference to the drawings of FIGS. 1 and 2, a tissue welder 10 in one embodiment of the present invention is shown to include a handle 11, and an elongate shaft 14, and a distal portion 16. This distal portion 16 includes a pair of opposing jaws 21 and 23 which are adapted to compress tissue 18, having outer surfaces 19 that define deep inner portions 20.

In the illustrated example, the compressed tissue 18 has the configuration of a tube where one side of the tube is compressed into a surface proximate relationship with the other side of the tube in order to occlude the tube. It will be appreciated that the invention is equally adapted to bond any two pieces of tissue disposed in a tissue proximate relationship.

One of the opposed jaws 21 is configured to have a plurality of penetrating members or needles 25. The opposite jaw 23 provides a stop or a contact member against which the penetrating members 25 can be moved. Energy is delivered to, and through, the penetrating members 25 in such a manner that the tissue 18 contacted by each penetrating member 25 is deformed at a cellular level and fused or welded.

Operation of the tissue welder 10 can be best understood with reference to the progressive side views of FIGS. 5A-5E and the associated progressive end views FIGS. 6A-6E, respectively.

Figure 5A:
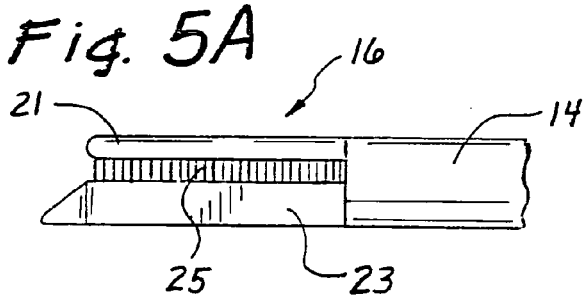
FIG. 5A is a side elevation view of the distal portion of the device showing the electrodes and connector in a closed condition.
Figure 5B:
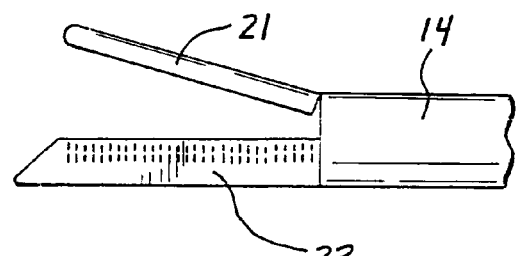
FIG. 5B is a side elevation view of the distal portion of the device showing the electrodes and connector in an open condition.
Figure 5C:
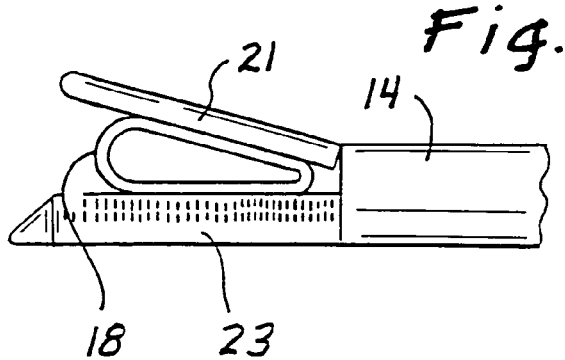
FIG. 5C is a side elevation view of the distal portion of the device showing electrodes and connector in an open, and tissue-receiving condition.
Figure 5D:
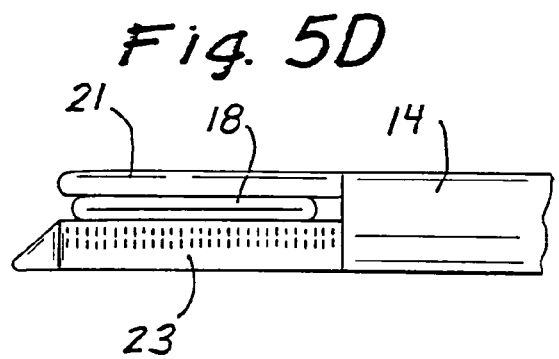
FIG. 5D is a side elevation view of the distal portion of the device showing the electrodes and connector in a closed, tissue-engaging condition.
Figure 6D:
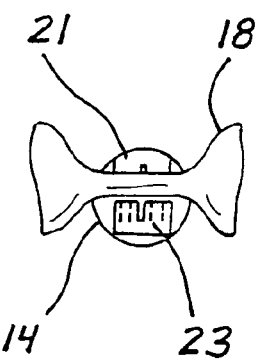
FIG. 6D is an end elevation view of the distal portion of the device shown in FIG. 5D.
Figure 5E:
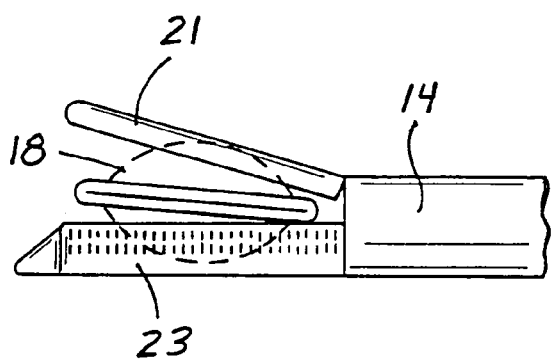
FIG. 5E is a side elevation view of the distal portion of the present invention showing the electrodes and connector in an open, tissue-releasing condition.
Figure 6E:
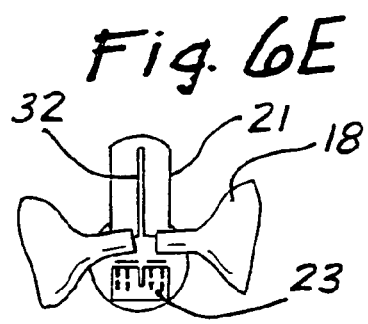
FIG. 6E is an end elevation view of the distal portion of the device shown in FIG. 5E.

More specifically, a portion of the tissue 18 is placed between the opposed jaws 21, 23 (FIGS. 5C and 6C) and lightly compressed (FIGS. 5D and 6D). As the compression occurs, the sharp needles 25 are urged through the compressed tissue 18 and into contact with, or in close proximity to, the opposing jaw 23. In one embodiment, electrical current is introduced through the needles 25. These needles 25 are made from an electrically high resistance material so that the electrical current produces heat. It follows that the tissue 18 in contact with the needles 25 is heated, preferably to a point where the cellular content is vaporized, and the protein components fused to form a contiguous structure through the tissue 18 adjacent to the needles 25. When the needles 25 are removed and the jaws opened (FIGS. 5E and 6E), a plurality of fused columns or channels remain with lumens which represent needle entry and exit points. In this embodiment, the fused columns are arranged in a pattern that is secure and fluid-flow arresting.

Figure 8:
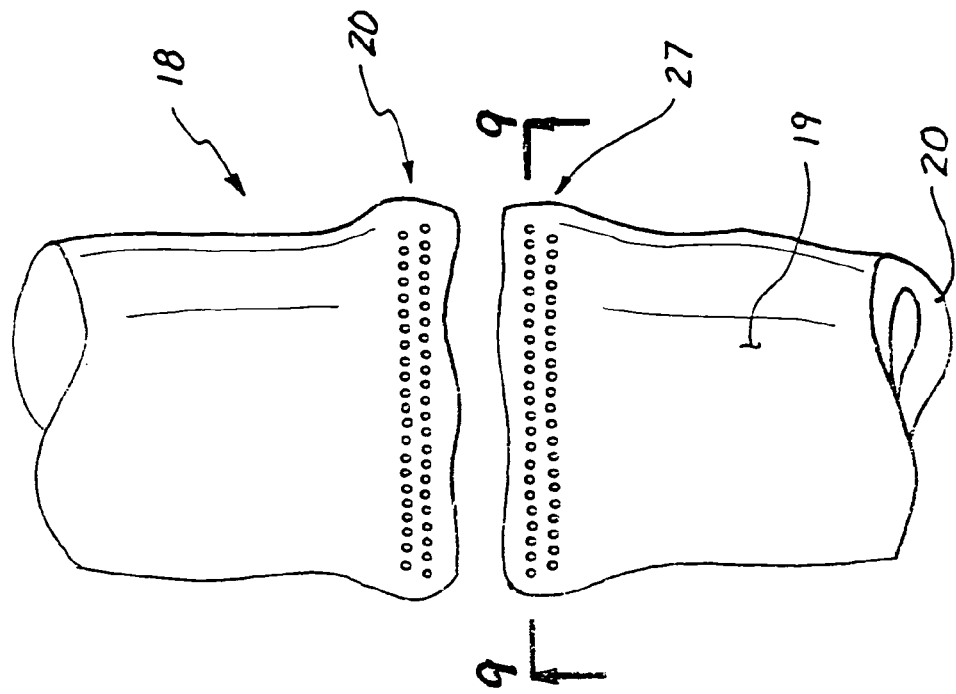
FIG. 8 is a top plan view of a portion of a body conduit that has been fused and divided using the present invention.
Figure 7:
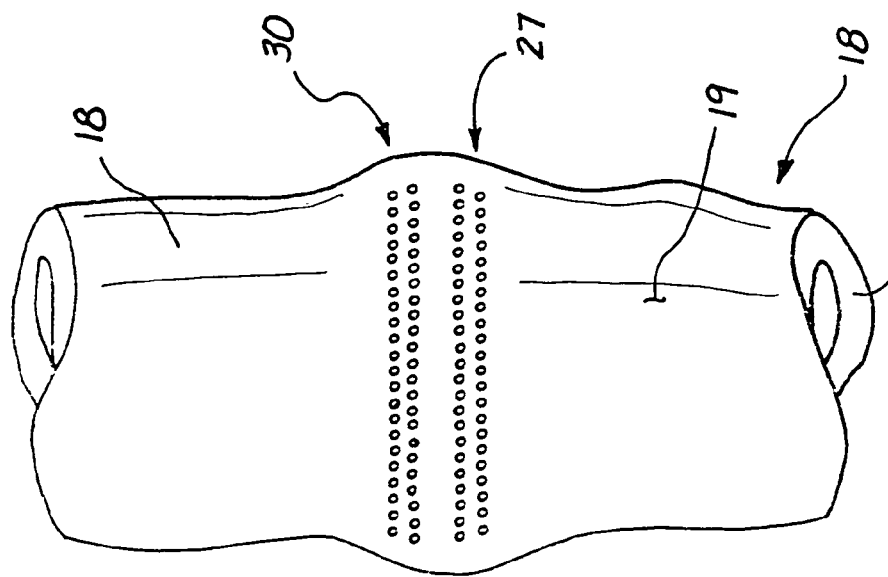
FIG. 7 is a top plan view of a portion of a body conduit that has been fused using the present invention.
Figure 9:
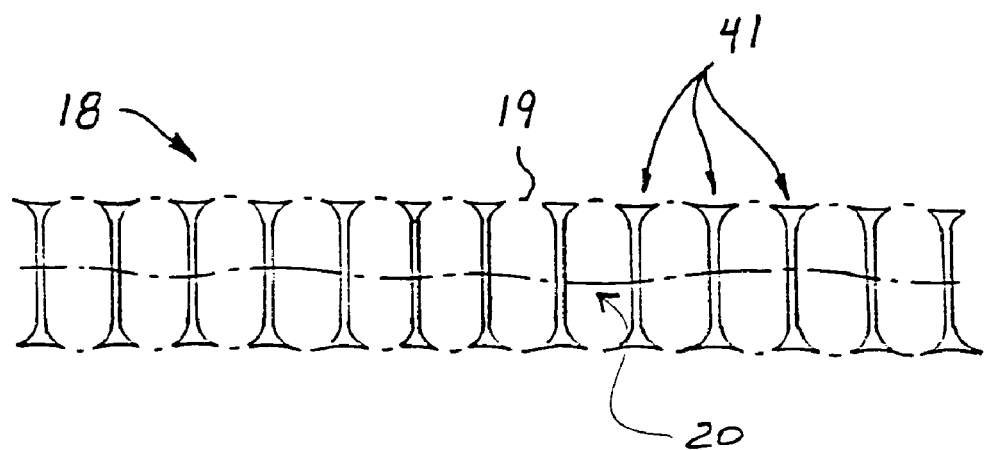
FIG. 9 is a cross section view of the fused or welded body conduit, taken along lines 9-9 of FIG. 8.
Figure 10:
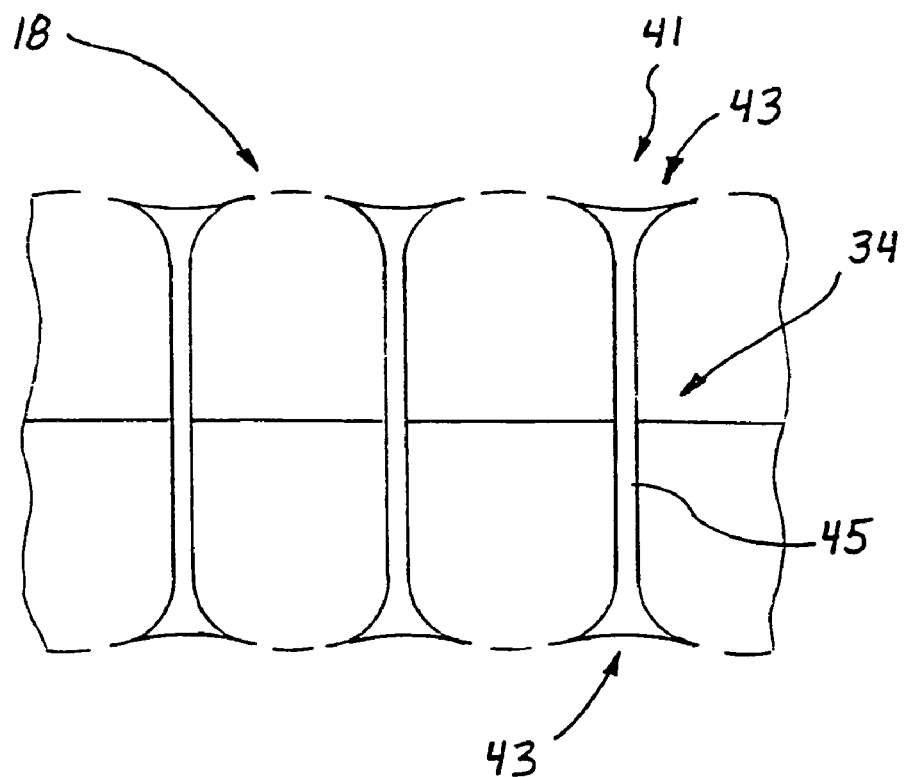
FIG. 10 is an enlarged view of the cross section illustrated in FIG. 9.

The pattern may include, for instance, a first group 27 of two or three closely spaced rows of fused columns, spaced apart from a second group 30 of two or three closely spaced rows of fused columns as illustrated in FIG. 7. A cutting or dividing member 32, in the form of a blade or an electrosurgical electrode, may be urged to divide the first group of rows 27 from the second group of rows 30 so as to sever the tissue 18 of the conduit, as illustrated in FIG. 8. These divided portions 36, 38 are each sealed in a fluid tight manner by the respective groups of fused columns 27, 30.

It will be appreciated that there are at least three considerations which might be addressed in dividing a body passage such as an artery, a vein or a portion of colon, intestine or bowel. A first consideration is that of sealing the lumen so that the contents of the body passage are not released in an uncontrolled manner. The second consideration is that blood flow from an incision or cut be arrested or at least minimized. A third consideration is that adequate nutrition can be maintained within the divided or residual portions 36, 38 of the affected tissue 18.

Figure 13:
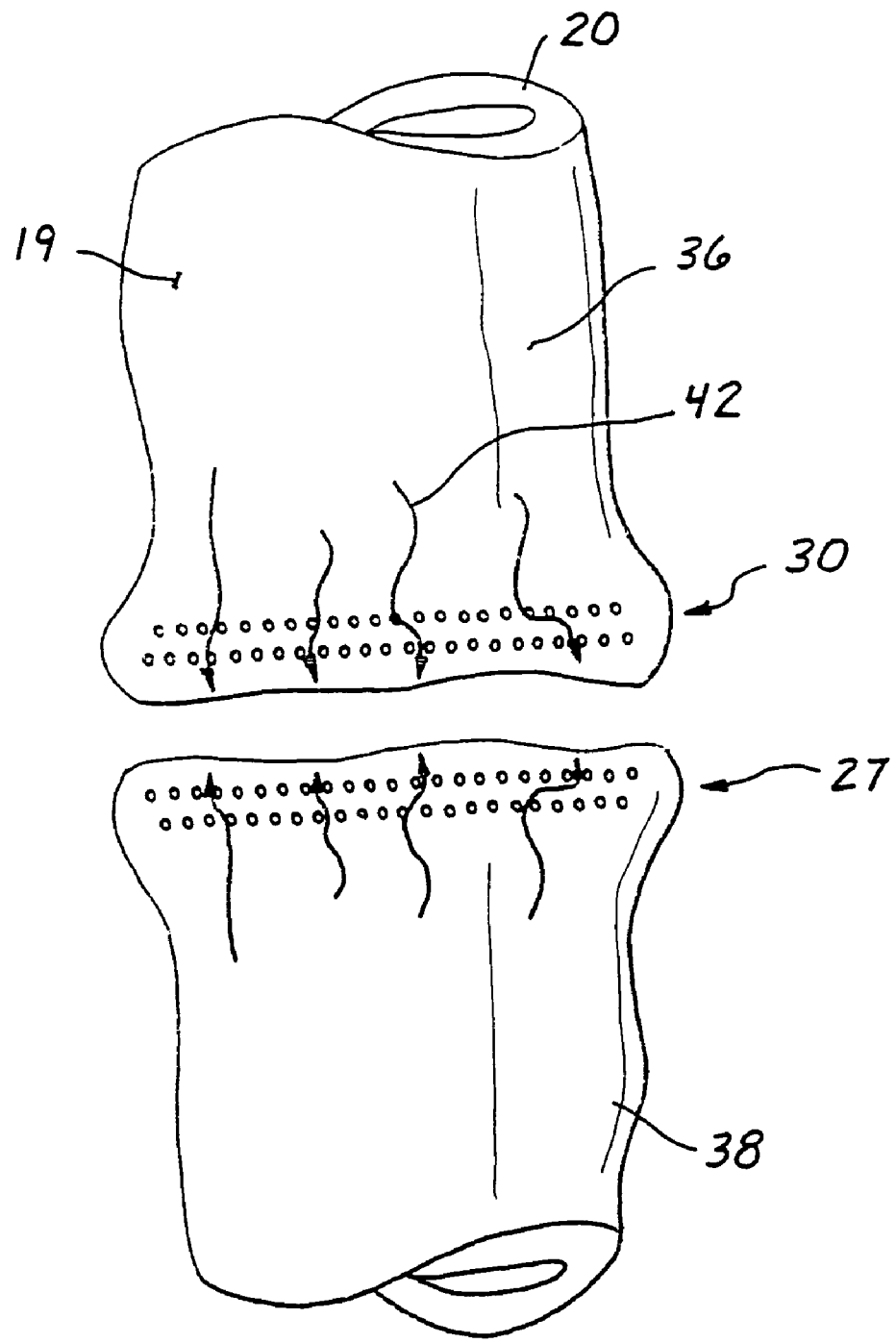
FIG. 13 is a top plan view similar to FIG. 8 and illustrating a nutritional pathway in a fused tissue portion.

Referring to FIGS. 9-13, fused columns 41 associated with the present invention are seen in an arrangement that provides a secure connection between the extreme tissue margins at intervals that permit nourishment flow 42 to the residual portions 36, 38 (FIG. 13). A closer look at the fused-columns 41 reveals that denatured cellular components have been fused or welded adjacent to the penetrating needles 25. The penetrating needles 25 heat the adjacent tissue only in the immediate area around the needles so that tissue further removed from the needles 25 remains in a natural condition.

Generally, a larger area 43 of thermal modification exists at each tissue surface 19, while a smaller area 45 of thermal modification exists at the larger and deeper portions 20 of the tissue 18. This provides the denatured column with an hourglass configuration. The sealing of the lumen 41 in the embodiment, requires only that the tissue be heated in proximity to the penetrating needles. For comparison, it will be noted that devices of the prior art rely on a transfer of thermal-energy through the entire portion of tissue indiscreetly. One advantage of this embodiment is that thermal energy is localized in order to maximize the health, vitality and perfusion of the remaining tissue.

Additional embodiments of the invention are illustrated in FIGS. 14-17. In these embodiments, the opposed jaws include the jaw 21 which has a fixed relationship with the elongate shaft 14, and the jaw 23 which is hinged to the jaw 21 and moveable relative to the shaft 14. The first jaw 21 may be sized and configured to receive a cartridge containing a plurality of the metallic penetrating needles 25 or electrodes. In the embodiment of FIG. 14, the needles 25 are in electrical continuity with one electrical pole of a direct-current power source 47. The second, movable jaw portion 23 is in electrical continuity with the opposite electrical pole of the same direct current power source 47. The penetrating needles 25, in the preferred embodiment, are made of a metal that exhibits high electrical resistance. As electricity flows through the circuit made by contacting the needles of the first jaw 21 with the contact surface of the second jaw 23, heat is generated within the needles 25. It should be noted that all of the needles 25 need not be energized simultaneously. In fact, sequential activation may be preferred as it diminishes the amount of energy required at any one time for the desired effect.

In the embodiment of FIG. 15, the tissue welder 10 is connected to an Electrosurgical Generator (ESG) 50. Most ESGs have a bipolar (BP) connection, a monopolar (MP) connection and a return-path (RP) connection. Coupling the welder 10 to the BP function of the ESG connects one pole of a current flow path to the jaw 21, and connects an opposite pole of the current flow path to the jaw 23.

A monopolar connection involves a ground plate 52 as illustrated in FIG. 16. In this embodiment, a high frequency, high voltage alternating current from the generator 50 flows between the poles and through the contacting needles 25 of the first jaw. The current density existing in the needles 25 causes them to become hot and fuse the tissue 18.

In the embodiment of FIG. 17, a heating element 54 is placed in contact with the penetrating needles 25. The heating element 54 may heat all of the penetrating needles together or may heat them sequentially or in groups such as rows. An electrical circuit or a mechanical motion may facilitate control of heat transfer to the penetrating needles. The selection of individual needles 25 or groups of needles will allow the included tissue to cool down between applications of heat through the tissue. The tissue 18 surrounding the fused-columns 41 will remain patent if it is not continuously exposed to the heat required to perform the fusion or tissue welding associated with the present invention.

Figure 18:
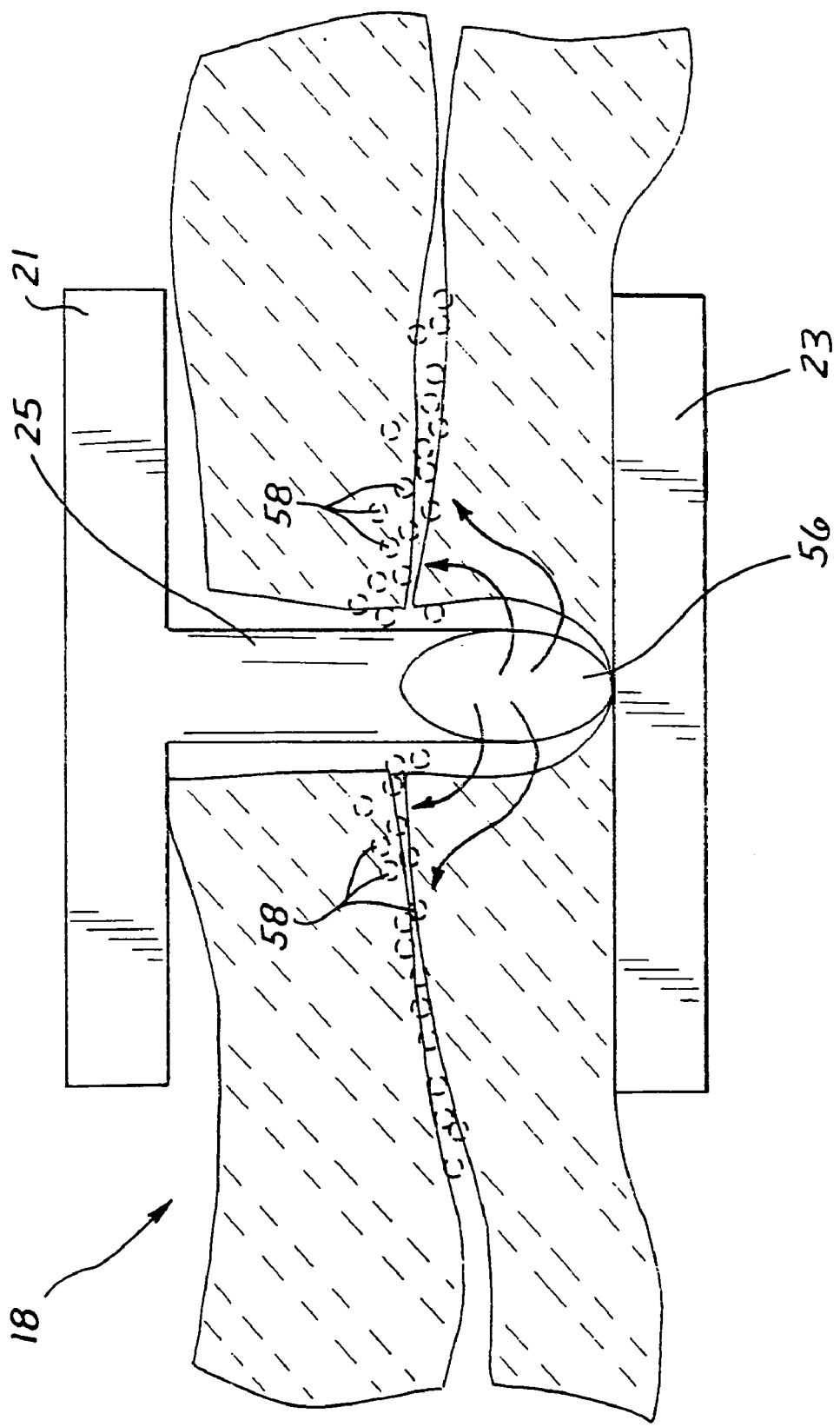
FIG. 18 is a side elevation view of a chemical releasing embodiment adapted for bonding enhancement.

With reference to FIG. 18, a surgical retractor is shown to include a first tissue-penetrating member, such as the jaw 21, and a second non-penetrating member, such as the jaw 23. The independent first and second members may be used to mobilize or move tissue, and to hold it in a preferred position or condition. The second member 21 may, subsequently, be placed in position on the opposite side of the target tissue. When appropriately positioned, the first and second members may be energized to create heat within the penetrating needles 25. The penetration sites form fused or welded columns through the target tissue.

An additional advantage of the present invention can be appreciated from the embodiment of FIG. 18 where a chemical releasing member 56 is placed upon each of the penetrating needles 25. As the needles 25 and the associated chemical releasing members 56 are forced into the tissue, a chemical 58 is drawn into the puncture sites. The chemical may include a thrombogenic material, a fibrogenic material, a coagulant, germicidal, anti-microbial material, an adhesive, or a lubricant material, for example. In a preferred embodiment, each of the chemical releasing members 56 contain a compressible foam that releases the chemical 58 as the foam is compressed.

An alternate embodiment of the present invention is seen in FIG. 19 where the first jaw 21 is fitted with a first group 60 of the tissue penetrating needles 25, and the second jaw 23 is fitted with a second group 61 of the tissue penetrating needles 25. The first group 60 of the needles is arranged so that they do not interfere with a second group 61 of the needles. This arrangement of the needles 25 leaves a pattern of fused or welded lumens that is most appropriate for security and fluid-stasis, and that permits appropriate nutrition to the residual tissue.

Referring to FIGS. 20 and 21, a mechanical cutting member 63 can be employed with the tissue fusing needles 25 of the present invention. After fusion or welding of the target tissue has occurred and appropriate fluid stasis is achieved, the mechanical cutting member 63 can be advanced along an arrow 65 to divide the two fused or welded portions of tissue. The cutting member 63 in the illustrated embodiment comprises a sharpened surgical blade that is straight, curved or angled, and that can be advanced or retracted as required.

An additional embodiment may include an electrosurgical cutting electrode 64 (ESE), as shown in FIG. 21. The ESE may be a wire, a blade, or a snare that is independently connected to the ESG 50. In the case of electrosurgical cutting, an electrosurgical coagulation mode or a blended waveform may be chosen that coagulates small remaining bleeders. Thus, the electrosurgical effect may be achieved independently of the electrode 64 with the heating of the penetrating needles 25. In an additional embodiment, the electrosurgical voltage may be broken-down or adjusted to perform the heating of the penetrating needles 25 prior to activation of the cutting electrode 64.

With reference to FIG. 22, particular attention is drawn to the potential of different embodiments to be sized and configured for use in "small-bore" laparoscopy. Either or both of the opposed jaws 21,23, can be fitted with the tissue penetrating needle group 60, 61, which can be energized and subsequently heated to fuse or weld tissue as previously disclosed. The force required to occlude a body passage is generally available in small-bore laparoscopic instruments. However, there is often insufficient room in a small-bore instrument to facilitate either the application or the formation of staples. The present invention replaces staples of the prior art, with electrical heating of specific regions of tissue to the point of cellular fusion.

The method and apparatus used to energize the electrodes in various embodiments of the invention may differ significantly. For example, in FIG. 23, a solid-state electronic switching arrangement 65 is illustrated for selectively energizing the electrodes or needles 25. The electrodes can be individually and sequentially energized and of course can be energized all at once. As illustrated in FIG. 23, small groups of the electrodes can be energized simultaneously with different groups being energized sequentially.

FIG. 24 illustrates a mechanical switching arrangement wherein an energizing block 67 is moved among the electrodes or needles 25 to activate those needles in contact with the block 67. In such an embodiment, the electrodes or needles 25 tend to be energized in small groups, and sequentially from one end of the jaw 21 to the other end of the jaw 21. In a similar embodiment illustrated in FIG. 25, the energizing block 67 is carried by a pusher 69 having an inclined plane 70. This plane 70 lifts the needles 25 from a withdrawn position to an exposed operative position, at which point the block 67 sequentially energizes the electrodes or needles 25.

Looking now to FIGS. 26 and 27, a method of providing continuous contact between the penetrating needles 25 of the first jaw 21 and the contact surface of the second jaw 23 is shown where the second jaw 23 comprises a "honey-combed" structure 72. This structure allows the penetrating needles to enter into the second jaw portion without compressive resistance. As the second jaw 23 is compressed upon tissue, the honeycombed structure 72 is drawn or pushed axially, as shown by an arrow 74 in FIG. 27, so that the penetrating needles are forced into electrical contact with the second jaw 23.

Figure 30:
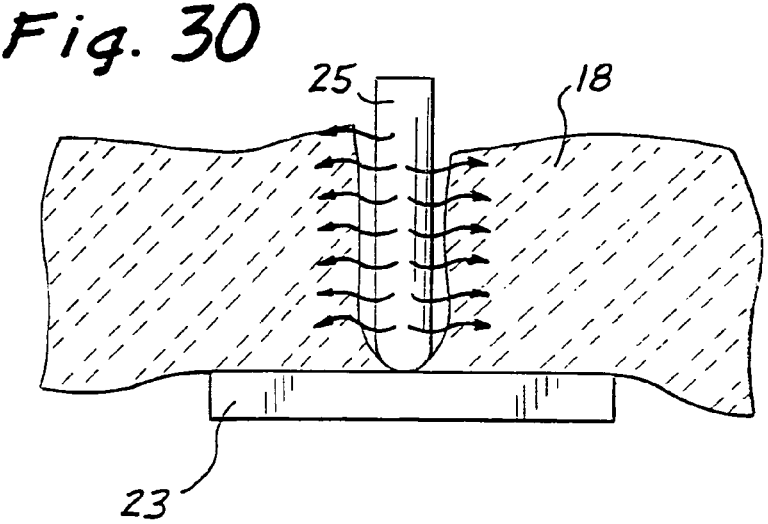
FIG. 30 is a side elevation view illustrating the direct heating of the penetrating needle.
Figure 29:
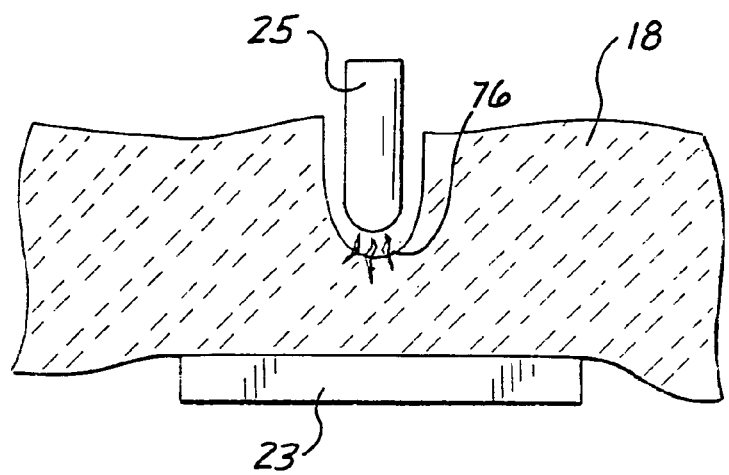
FIG. 29 is a side elevation view illustrating electrosurgical cutting and heating of a penetrating needle.
Figure 28:
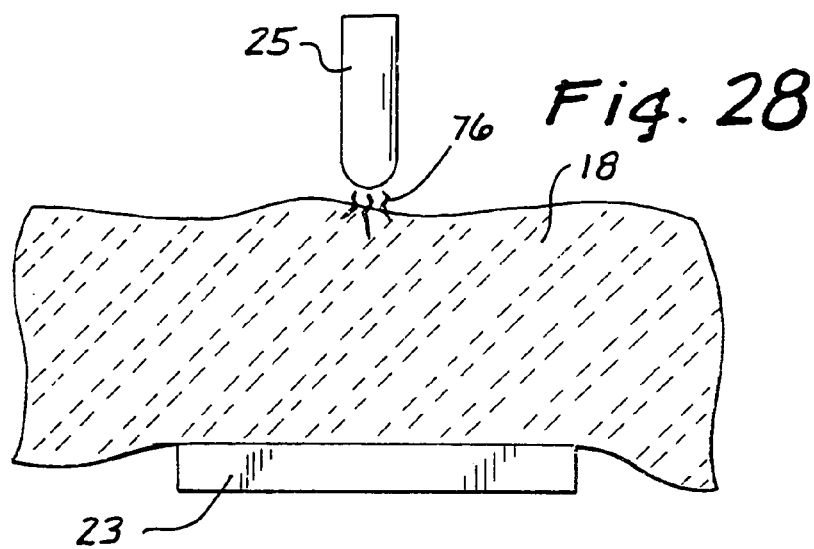
FIG. 28 is a side elevation view illustrating radio frequency electrosurgical cutting with a penetrating needle.

FIGS. 28-30 illustrate schematically the effect which electrosurgery and/or heat has on the compressed tissue 18. The application of high frequency electrosurgical waveforms 76 will vaporize the fluid within the cells of compressed tissue and cause them to literally explode. A blended signal that includes an overwritten waveform, will provide hemostasis or coagulation as the cutting occurs. In addition to the cutting and coagulation, heat, whether generated indirectly by electrosurgical current flow or directly by heating of an element, tends to dry the tissue and denatures the cellular structures. In the present context, this heat produces a denatured column which defines the continuous lumen 41 through the tissue 18.

With reference to FIGS. 31-34, a hemostatic clamp 76 is shown configured generally as a scissors-like device. The opposed tissue contacting surfaces are configured with tissue penetrating needle members 25, 61 adapted to penetrate interposed tissue. An electrosurgical instrument, either monopolar 78 (FIG. 34) or bipolar 81 (FIG. 33), may be used to contact the hemostatic clamp 76 and deliver current flow through it. A direct heat source 83 (FIG. 32) or an external source 85 could also be used. Discharge of this energy creates heat in the small diameter needles 25, 61 where the current density is elevated.

A close look at FIG. 35 reveals that a further embodiment may include a plurality of tissue penetrating needles 25 that are urged into and through tissue to be adhered. The needles 25 are configured to allow a small flow of blood into the puncture sites. The blood coagulates and forms a glue-like substance when mixed with other chemical components introduced to the site for example by a disposable chemical releasing sleeve 87. The jaw 23 can be covered by the sleeve 87 to provide increased continuity with the jaw 23 and the tissue 18.

Figure 36:
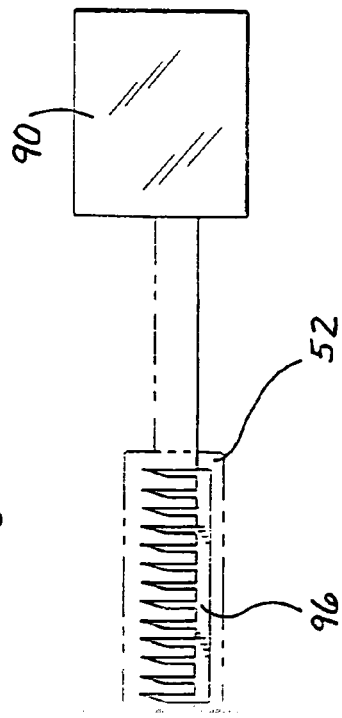
FIG. 36 is a side elevation perspective view of a distal jaw portion arranged in a monopolar electrosurgical configuration.

Standard electrical schematics are seen in FIG. 36 where it is shown that an ES generator "monopolar" circuit 90 comprises an active electrode 96 and a passive electrode or "grounding-pad" 52. The current density at the active electrode 96 contact site is substantially greater than the current density at the attachment site of the passive electrode. For example, in a typical arrangement, the current density of the active electrode contact area might be two thousand times greater than the current density at the passive electrode site. The elevated current density relationship produces a spark at the site of contact or near contact of the active electrode 96 with the tissue 18. However, the return path of the current flow is dissipated, dispersed or diluted due to the larger surface area of the return electrode or grounding pad 52.

Figure 37:
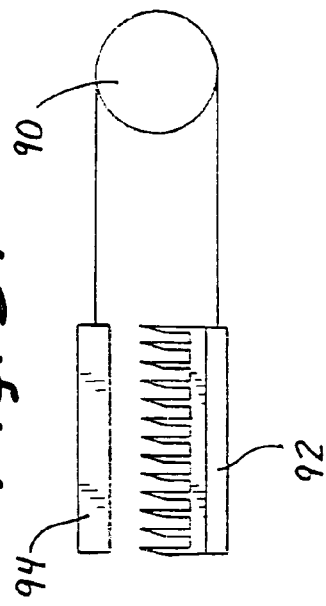
FIG. 37 is a side elevation schematic view of a distal jaw portion arranged in a bipolar electrosurgical configuration.

The bipolar arrangement, shown schematically in FIG. 37, provides an electrical potential between two nearly identical active electrodes 92, 94. The current density associated with the two electrodes 92, 94 is nearly the same. Tissue may be grasped, for instance between the two bipolar electrodes 92, 94, and cut and coagulated without the patient being a part of the electrical circuit as is the case with monopolar electrosurgery.

Figure 38:
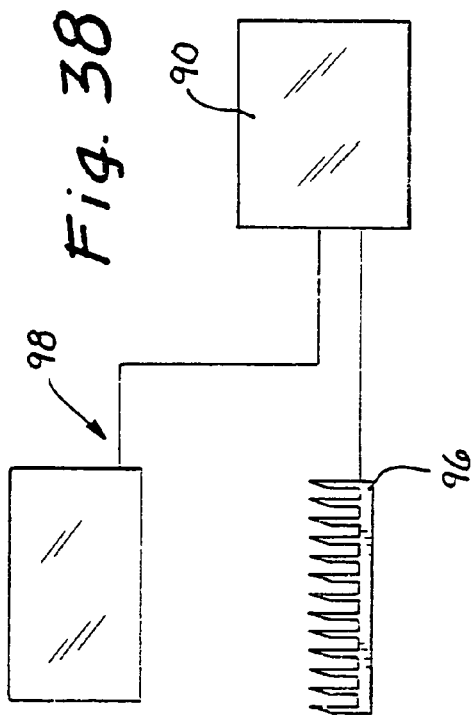
FIG. 38 is a side elevation schematic view of a distal jaw portion arranged in a "quasi" bipolar electrosurgical configuration.

A hybrid form of electrosurgery is illustrated in FIG. 38 where an active electrode 96 is positioned adjacent to a return electrode path 98 upon a single instrument. To illustrate, an instrument having a metal shaft and an insulated metal electrode works by providing high current density at the active electrode 96 and less current density on the return path 98.

Figure 39:
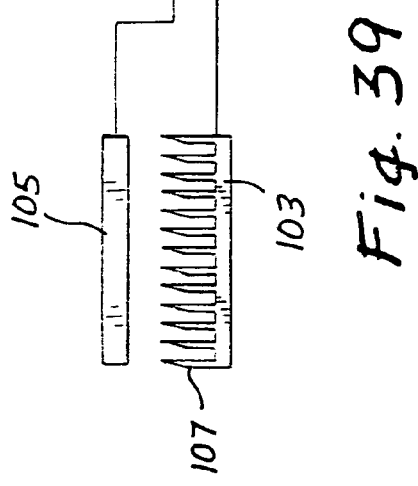
FIG. 39 is a side elevation schematic view of a distal jaw portion arranged with a direct current, resistance-type configuration.

A more simple approach, illustrated schematically in FIG. 39, involves use of direct current (D-C) such as that derived from a battery or rectifier 101. This D-C apparatus supplies one pole to one electrode members 103 and the opposite pole to the opposite electrode member 105. Needles 107, in the form of resistive electrode members communicate between the poles and generate heat.

It will be understood that many other modifications can be made to the various disclosed embodiments without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of the embodiments. Those skilled in the art will envision other modifications within the scope and spirit of the present invention as defined by the following claims.

The invention claimed is:

1. A tissue welding apparatus for fusing a first piece of tissue in a surface proximate relationship with a second piece of tissue, comprising:
    an operative member adapted to be disposed generally on a side of the first piece of tissue opposite the second piece of tissue;
    at least one penetrating member movable with the operative member relative to the first piece of tissue, the penetrating member being adapted to penetrate the first piece of tissue and the second piece of tissue;
    the penetrating member being adapted for connection to a source of heat for heating the penetrating member in order to form a tissue weld bonding the first piece of tissue to the second piece of tissue;
    a chemical agent carried by the penetrating member on an exterior surface of the penetrating member, at least a portion of the chemical agent adapted to be released when the penetrating member penetrates at least one of the first piece of tissue and the second piece of tissue to facilitate a reaction between the chemical agent and at least one of the first piece of tissue and the second piece of tissue;
    an elongate shaft, the operative member being a first jaw connected to the elongate shaft; and
    a second jaw connected to the shaft in an opposing relationship with the first jaw, the first jaw movable towards the second jaw;
    wherein the at least one penetrating member comprises a plurality of needles affixed to a substantially planar surface of the first jaw; and
    further comprising an energizing block movable longitudinally along the first jaw electrically coupling a subset of the plurality of needles to the source of heat.

2. The apparatus recited in claim 1, further comprising:
    a chemical releasing member disposed on the at least one penetrating member and having properties for carrying the chemical agent.

3. The apparatus recited in claim 1, wherein the chemical agent has properties for producing a mechanical reaction with at least one of the first piece of tissue and the second piece of tissue.

4. The apparatus recited in claim 3, wherein the chemical agent includes at least one of an adhesive, a lubricant, and a coagulant.

5. The apparatus recited in claim 1, wherein the chemical agent has properties for producing a chemical reaction with at least one of the first piece of tissue and the second piece of tissue.

6. The apparatus recited in claim 5, wherein the chemical agent includes at least one of a thrombogenic, fibrogenic, germicidal, and microbial material.

7. The apparatus recited in claim 1, wherein the at least one penetrating member comprises the plurality of needles each integrated with a corresponding chemical releasing portion supplying the chemical agent.

8. The apparatus recited in claim 1, wherein the source of heat comprises a direct current electrical power source.

9. The apparatus recited in claim 1, wherein the second jaw comprises a continuous flat planar surface along an entire length of the second jaw facing the first jaw.

10. The apparatus recited in claim 1, wherein each of the plurality of needles comprise an electrosurgical electrode.

11. The apparatus recited in claim 1, wherein the second jaw comprises an electrosurgical electrode.

12. The apparatus recited in claim 1, further comprising a solid state energy source and wherein each of the plurality of needles is an individual electrode selectable to receive electrical energy from the solid state energy source.

13. The apparatus recited in claim 1, wherein the second jaw comprises a plurality of apertures facing the plurality of needles on the opposing first jaw.

14. The apparatus recited in claim 13, wherein the second jaw is movable in a first direction towards the first jaw positioning each of the plurality of needles into an associated aperture of the plurality of apertures of the second jaw.

15. The apparatus of claim 14 wherein the second jaw is movable along a second direction being different from the first direction, each of the plurality of needles inserted into the associate aperture of the plurality of apertures contacting portions of each of the plurality of apertures of the second jaw.

16. A tissue welding apparatus for fusing a first piece of tissue in a surface proximate relationship with a second piece of tissue, comprising:
    an operative member adapted to be disposed generally on a side of the first piece of tissue opposite the second piece of tissue;

at least one penetrating member movable with the operative member relative to the first piece of tissue, the penetrating member being adapted to penetrate the first piece of tissue and the second piece of tissue;

the penetrating member being adapted for connection to a source of heat for heating the penetrating member in order to form a tissue weld bonding the first piece of tissue to the second piece of tissue;

a chemical agent carried by the penetrating member on an exterior surface of the penetrating member, at least a portion of the chemical agent adapted to be released when the penetrating member penetrates at least one of the first piece of tissue and the second piece of tissue to facilitate a reaction between the chemical agent and at least one of the first piece of tissue and the second piece of tissue;

an elongate shaft, the operative member being a first jaw connected to the elongate shaft;

a second jaw connected to the shaft in an opposing relationship with the first jaw, the first jaw movable towards the second jaw;

wherein the at least one penetrating member comprises a plurality of needles affixed to a substantially planar surface of the first jaw; and further comprising an energizing block movable from a proximal position to a distal position and sequentially supplying electrical energy to groups of the plurality of needles along the first jaw.

17. The apparatus recited in claim 16, further comprising:
a chemical releasing member disposed on the at least one penetrating member and having properties for carrying the chemical agent.

18. The apparatus recited in claim 16, wherein the chemical agent has properties for producing a mechanical reaction with at least one of the first piece of tissue and the second piece of tissue.

19. The apparatus recited in claim 18, wherein the chemical agent includes at least one of an adhesive, a lubricant, and a coagulant.

20. The apparatus recited in claim 16, wherein the chemical agent has properties for producing a chemical reaction with at least one of the first piece of tissue and the second piece of tissue.

21. The apparatus recited in claim 20, wherein the chemical agent includes at least one of a thrombogenic, fibrogenic, germicidal, and microbial material.

22. The apparatus recited in claim 16, wherein the at least one penetrating member comprises the plurality of needles each integrated with a corresponding chemical releasing portion supplying the chemical agent.

23. The apparatus recited in claim 16, wherein the source of heat comprises a direct current electrical power source.

24. The apparatus recited in claim 16, wherein the second jaw comprises a continuous flat planar surface along an entire length of the second jaw facing the first jaw.

25. The apparatus recited in claim 16, wherein each of the plurality of needles comprise an electrosurgical electrode.

26. The apparatus recited in claim 16, wherein the second jaw comprises an electrosurgical electrode.

27. The apparatus recited in claim 16, further comprising a solid state energy source and wherein each of the plurality of needles is an individual electrode selectable to receive electrical energy from the solid state energy source.

28. The apparatus recited in claim 16, wherein the second jaw comprises a plurality of apertures facing the plurality of needles on the opposing first jaw.

29. The apparatus recited in claim 28, wherein the second jaw is movable in a first direction towards the first jaw positioning each of the plurality of needles into an associated aperture of the plurality of apertures of the second jaw.

30. The apparatus of claim 29 wherein the second jaw is movable along a second direction being different from the first direction, each of the plurality of needles inserted into the associate aperture of the plurality of apertures contacting portions of each of the plurality of apertures of the second jaw.

31. A tissue welding apparatus for fusing a first piece of tissue in a surface proximate relationship with a second piece of tissue, comprising:
an operative member adapted to be disposed generally on a side of the first piece of tissue opposite the second piece of tissue;

at least one penetrating member movable with the operative member relative to the first piece of tissue, the penetrating member being adapted to penetrate the first piece of tissue and the second piece of tissue; and the at least one penetrating member comprising a plurality of needles affixed to a substantially planar surface of the first jaw the penetrating member being adapted for connection to a source of heat for heating the penetrating member in order to form a tissue weld bonding the first piece of tissue to the second piece of tissue;

an energizing block movable longitudinally along the first jaw electrically coupling a subset of the plurality of needles to the source of heat; and a chemical agent carried by the penetrating member to facilitate a reaction between the chemical agent and at least one of the first piece of tissue and the second piece of tissue.

32. The apparatus recited in claim 31, further comprising:
a chemical releasing member disposed on the at least one penetrating member and having properties for carrying the chemical agent.

33. The apparatus recited in claim 31, wherein the chemical agent has properties for producing a mechanical reaction with at least one of the first piece of tissue and the second piece of tissue.

34. The apparatus recited in claim 33, wherein the chemical agent includes at least one of an adhesive, a lubricant, and a coagulant.

35. The apparatus recited in claim 31, wherein the chemical agent has properties for producing a chemical reaction with at least one of the first piece of tissue and the second piece of tissue.

36. The apparatus recited in claim 35, wherein the chemical agent includes at least one of a thrombogenic, fibrogenic, germicidal, and microbial material.

37. The apparatus recited in claim 31, wherein the at least one penetrating member comprises the plurality of needles each integrated with a corresponding chemical releasing portion supplying the chemical agent.

38. The apparatus recited in claim 31, wherein the source of heat comprises a direct current electrical power source.

39. The apparatus recited in claim 31, wherein the second jaw comprises a continuous flat planar surface along an entire length of the second jaw facing the first jaw.

40. The apparatus recited in claim 31, wherein each of the plurality of needles comprise an electrosurgical electrode.

41. The apparatus recited in claim 31, wherein the second jaw comprises an electrosurgical electrode.

42. The apparatus recited in claim 31, further comprising a solid state energy source and wherein each of the plurality of needles is an individual electrode selectable to receive electrical energy from the solid state energy source.

43. The apparatus recited in claim 31, wherein the second jaw comprises a plurality of apertures facing the plurality of needles on the opposing first jaw.

44. The apparatus recited in claim 43, wherein the second jaw is movable in a first direction towards the first jaw positioning each of the plurality of needles into an associated aperture of the plurality of apertures of the second jaw.

45. The apparatus of claim 44 wherein the second jaw is movable along a second direction being different from the first direction, each of the plurality of needles inserted into the associate aperture of the plurality of apertures contacting portions of each of the plurality of apertures of the second jaw.

46. A tissue welding apparatus for fusing a first piece of tissue in a surface proximate relationship with a second piece of tissue, comprising:
    an operative member adapted to be disposed generally on a side of the first piece of tissue opposite the second piece of tissue;
    at least one penetrating member movable with the operative member relative to the first piece of tissue, the penetrating member being adapted to penetrate the first piece of tissue and the second piece of tissue; and the at least one penetrating member comprising a plurality of needles affixed to a substantially planar surface of the first jaw
    the penetrating member being adapted for connection to a source of heat for heating the penetrating member in order to form a tissue weld bonding the first piece of tissue to the second piece of tissue;
    an energizing block movable from a proximal position to a distal position and sequentially supplying electrical energy to groups of the plurality of needles along the first jaw; and
    a chemical agent carried by the penetrating member to facilitate a reaction between the chemical agent and at least one of the first piece of tissue and the second piece of tissue.

47. The apparatus recited in claim 46, further comprising:
    a chemical releasing member disposed on the at least one penetrating member and having properties for carrying the chemical agent.

48. The apparatus recited in claim 46, wherein the chemical agent has properties for producing a mechanical reaction with at least one of the first piece of tissue and the second piece of tissue.

49. The apparatus recited in claim 48, wherein the chemical agent includes at least one of an adhesive, a lubricant, and a coagulant.

50. The apparatus recited in claim 46, wherein the chemical agent has properties for producing a chemical reaction with at least one of the first piece of tissue and the second piece of tissue.

51. The apparatus recited in claim 50, wherein the chemical agent includes at least one of a thrombogenic, fibrogenic, germicidal, and microbial material.

52. The apparatus recited in claim 46, wherein the at least one penetrating member comprises the plurality of needles each integrated with a corresponding chemical releasing portion supplying the chemical agent.

53. The apparatus recited in claim 46, wherein the source of heat comprises a direct current electrical power source.

54. The apparatus recited in claim 46, wherein the second jaw comprises a continuous flat planar surface along an entire length of the second jaw facing the first jaw.

55. The apparatus recited in claim 46, wherein each of the plurality of needles comprise an electrosurgical electrode.

56. The apparatus recited in claim 46, wherein the second jaw comprises an electrosurgical electrode.

57. The apparatus recited in claim 46, further comprising a solid state energy source and wherein each of the plurality of needles is an individual electrode selectable to receive electrical energy from the solid state energy source.

58. The apparatus recited in claim 46, wherein the second jaw comprises a plurality of apertures facing the plurality of needles on the opposing first jaw.

59. The apparatus recited in claim 58, wherein the second jaw is movable in a first direction towards the first jaw positioning each of the plurality of needles into an associated aperture of the plurality of apertures of the second jaw.

60. The apparatus of claim 59 wherein the second jaw is movable along a second direction being different from the first direction, each of the plurality of needles inserted into the associate aperture of the plurality of apertures contacting portions of each of the plurality of apertures of the second jaw.

* * * * *